Figure 1:
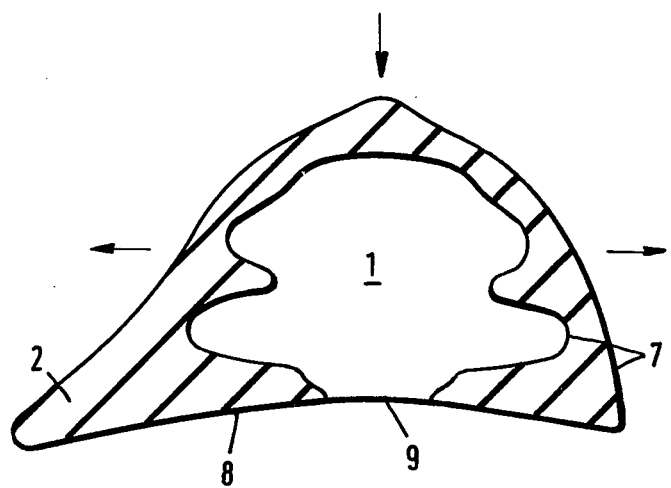

United States Patent [19]

Schaper et al.

[11] 4,184,214
[45] Jan. 22, 1980

[54] MAMMA PROSTHESIS AND MOLD FOR THE MANUFACTURE THEREOF

[75] Inventors: Gustav Schaper, Hanover; Gertraud Prahl nee Strassmeier, Rullstorf, both of Fed. Rep. of Germany

[73] Assignee: Traudl Prahl, Rullstorf, Fed. Rep. of Germany

[21] Appl. No.: 841,952

[22] Filed: Oct. 13, 1977

[30] Foreign Application Priority Data

Nov. 4, 1976 [DE] Fed. Rep. of Germany ....... 2650489

[51] Int. Cl.$^2$ .............................................. A61F 1/24
[52] U.S. Cl. ........................................ 3/36; 128/463; 249/55; 249/114 R; 249/142; 264/267; 264/338
[58] Field of Search ...................... 3/36; 128/463, 464, 128/479–481; 249/55, 112, 114, 115, 142; 264/222, 267, DIG. 30, 338

[56] References Cited

U.S. PATENT DOCUMENTS

| 2,543,499 | 2/1951 | Kausch | 3/36 X |
| 2,851,692 | 9/1958 | Livingston et al. | 3/36 UX |
| 3,067,431 | 12/1962 | Kausch | 3/36 |

FOREIGN PATENT DOCUMENTS

| 837000 | 4/1952 | Fed. Rep. of Germany | 3/36 |
| 804001 | 11/1958 | United Kingdom | 128/481 |

Primary Examiner—Clifford D. Crowder
Attorney, Agent, or Firm—Toren, McGeady and Stanger

[57] ABSTRACT

An artificial mamma having characteristics similar to a natural mamma consisting of a molded body made of a homogeneous resilient plastic material, the molded body being substantially closed but for a relatively small bottle neck shaped orifice at its human body engaging surface, and enclosing an internal cavity in the configuration of a thrust type cup spring for providing a certain resiliency and oscillation behavior and for compensating axial and radial forces.

4 Claims, 2 Drawing Figures

U.S. Patent  Jan. 22, 1980  4,184,214

MAMMA PROSTHESIS AND MOLD FOR THE MANUFACTURE THEREOF

The present invention relates generally to the field of artificial limbs and particularly to an artificial mamma or mamma prosthesis for women having undergone a mamma amputation wherein this artificial mamma is made of a resilient plastic material and includes a functional cavity.

In recent years the number of mamma-amputated women requiring artificial mammas has steadily increased. An amputation is in most cases the only remedy for removing malignant tumors. In dependence upon the size of the tumor spread, the amputation surgery will lead to scars of different sizes, and quite often insufficiently covered body surfaces will remain. In the course of a ray therapy that will be administered in most cases after the surgery, the scars often develop a hyper-sensitivity to pressure-applying edges and chafing points. Concurrently, the mamma amputation disturbs the symmetrical weight distribution on the vertibral column. The following four listed basic requirements must be met by an efficient mamma prosthesis:

(1) The prosthesis must be adapted as much as possible to the shape of the human body and include a largely closed body engaging surface at its side facing the human body.

(2) The weight of the mamma prosthesis must be selected so as to correspond substantially to the weight of its counterpart, i.e. the fully retained natural mamma in most cases. In this context, especially modifications in the scapular region and at the vertebral column must be avoided.

(3) The volume of the mamma prosthesis must be distributed in a manner so that the vibration behaviour of the artificial mamma is rather similar to the one of the natural mamma, or in other words, the artificial mamma must be compressible under the application of pressure forces, and must allow oscillating movements in a vertical direction similar to the movements of a natural mamma when the woman walks or runs. These movements should likewise serve to reduce displacements of the mamma with respect to the surface of the scar.

(4) Additionally, attention must be paid to the fact that the surfaces of mamma prostheses of this type consist of a physiologically neutral or compatible material since the scars quite often include "open" patches.

Prior Art.

For many years, there have been manufactured mamma prostheses of very different materials. Mamma prostheses made of sponge rubber and/or foam rubber have been known for several years. These heretofore known prostheses exhibit especially the drawback of not complying with the weight balancing requirements. More recently there have been made liquid filled bust prostheses of polyethylene sheet. It was observed, however, that during longer use the liquid tended to escape through the walls of the sheet since the sheet material employed was not allowed to exceed a certain thickness. Furthermore, these heretofore known mamma prostheses tend to collapse under their proper weight on the body of the wearer in a vertical direction, in forming a plurality of folds. There are also known mamma prostheses made of a resilient plastic material (a homogeneous plastic material, no foam material) including a cavity at the engagement surface. Prostheses of this cup-shaped type likewise do not meet important requirements of a mamma prosthesis. Thus are solved insufficiently especially the problems of the body engaging surface and of the vertical oscillation compensation, and these problems are especially important in more voluminous mamma shapes.

The prior art is documented by the following patents and utility models:
German Pat. No.: 837,000;
German Pat. No.: 1,303,139;
U.S Pat. No.: 2,851,692;
German Utility Model: 1,739,612;
German Utility Model: 7,603,424;
U.S. Pat. No.: 2,543,499.

It is the object of the present invention to provide a novel and improved mamma prosthesis for women wherein the above indicated four general requirements have been taken care of by technical design characteristics.

In accordance with the present invention, this object is achieved in the manufacture of a mamma-shaped molded body of a resilient plastic material of a specific weight of about 1, this molded body including an internal cavity in the shape of a thrust type cup spring for providing the required dampening characteristics in horizontal and vertical directions. This functional cavity concurrently includes only a small orifice in a bottle-neck shaped restriction at its body engaging surface.

Figure 2:
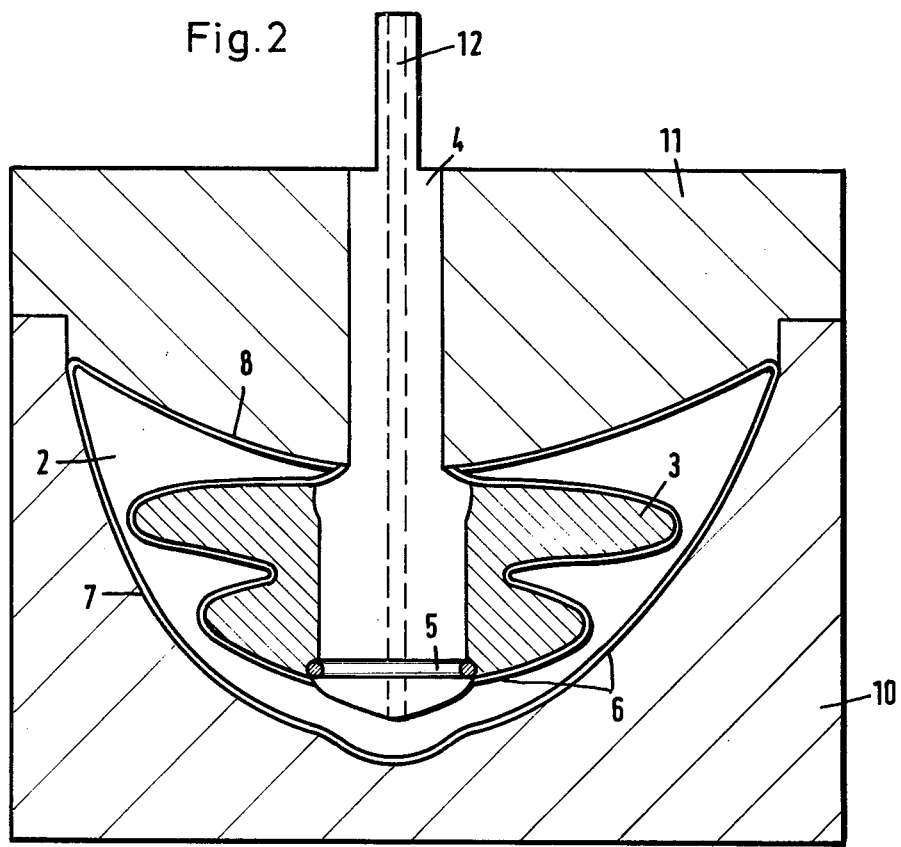

In the following, the present invention will be described more in detail with reference to the appended drawing wherein FIG. 1 is a vertical sectional view of a finished mamma prosthesis in accordance with present invention, and FIG. 2 is a similar view of a mamma prosthesis in a mold during the manufacturing process.

The artificial mamma shown in a vertical sectional view in FIG. 1 consists of a molded body having an internal cavity in the shape of a thrust type cup spring 1. This thrust type cup spring 1 allows oscillations of the mamma body in a vertical direction and furthermore to compress the artificial mamma without leading to increased pressure forces against the body along the body engaging surface 8. The body engaging surface may, therefore, be made flexible so as to adapt itself to the scar that is left upon amputation of the mamma. An aperture 9 extends through the body engaging surface 8 into the internal cavity. The internal cavity has two intercommunicating spaces with the space closer to the aperture 9 being larger in cross sectional area transverse to the direction of extent of the cavity from the aperture toward the opposite exterior surface than the other space. Each space is curved so as to be concave in the direction of the cavity from the aperture toward the opposite exterior surface.

Referring to FIG. 2, there is shown a mold 10 with an upper mold member 11. Mold and mold member define conjointly an enclosed mamma molding cavity. A core model 4 is inserted into the upper mold member 11. The core model 4 includes an annular groove 5 at its lower end. A commercially available latex bag 6 is attached to this annular groove 5. Subsequently a twin rib annular body 3 made of a resilient material is slidably engaged on the core model 4 and into the annular groove 5. This twin rib annular body 3 may be of any of several suitable different shapes that are selected in accordance with the size of the mamma. The latex bag 6 is then evacuated by a vacuum source (not shown) connected to the bag 6 by the conduit 12 in the core model 4. After evacuation, a fluid two-component plastic material adapted to cure by additional cross-linkage is introduced into the mold cavity through this conduit 12. The amount of material introduced into the mold is selected so that the latex bag 6 evenly engages the inner and outer mold regions. In this manner, inner and outer mold will be covered by the enclosing skin 7 of the latex bag 6. When the curing of the mold material is completed, the mold members are separated and the twin rib annular body 3 is removed from the molded body. The molded body 2 then includes this thrust type cup spring internal cavity 1.

It is apparent from the foregoing that a new an improved mamma prosthesis has been provided. While only one presently preferred embodiment has been described, as will be apparent to those familiar with the art, certain changes and modifications can be made without departing from the scope of the invention as defined by the following claims.

What is claimed is:

1. Mamma prosthesis comprising a molded hollow prosthesis body formed of a resilient plastic material and having an internal cavity therein, said body having a first exterior surface shaped to fit against the body of the wearer and a second exterior surface having a configuration corresponding to the shape of a natural mamma and projecting outwardly from said first surface when worn, said first surface having an aperture therethrough communicating with the internal cavity within said hollow prosthesis body, said aperture comprising a bottle-neck shaped opening into the internal cavity, wherein the improvement comprises that the hollow prosthesis body comprises an inner surface defining the internal cavity with the internal cavity extending from the aperture in said first exterior surface toward and spaced inwardly from said second exterior surface, and said inner surface having the configuration of a thrust type cup spring with the inner surface defining at least one inwardly projecting annular rib located intermediate and in spaced relation to the aperture and to the oppositely disposed portion of said inner surface and dividing the internal cavity into two intercommunicating spaces with the space closer to the aperture having a larger cross sectional area transverse to the direction of the cavity from the aperture toward said second exterior surface than the other space, and said inner surface having an arcuate configuration in the direction of the cavity from the aperture toward said second exterior surface and with said inner surface in each of said spaces being concave in the direction of the cavity from the aperture toward said second exterior surface.

2. Mamma prosthesis, as set forth in claim 1, wherein a bag-like casing formed of latex forms a lining completely covering said first surface, said second surface and said inner surface.

3. Mamma prosthesis comprising a molded hollow prosthesis body formed of a resilient plastic material and having an internal cavity therein, said body having a first exterior surface shaped to fit against the body of the wearer and a second exterior surface having a configuration corresponding to the shape of a natural mamma and projecting outwardly from said first surface when worn, said first surface having an aperture therethrough communicating with the internal cavity within said hollow prosthesis body, wherein the improvement comprises that said hollow prosthesis body comprises an inner surface defining the internal cavity, said inner surface having the configuration of a thrust type cup spring with the inner surface defining an inwardly projecting annular rib located intermediate and in spaced relation to the aperture and the oppositely disposed portion of said inner surface and dividing the interior cavity into two intercommunicating spaces, said inner surface as it extends from the aperture in the direction from said first surface toward said second surface initially diverges outwardly from said aperture to a maximum diameter spaced inwardly from said second surface and then converges inwardly forming a first portion of the internal cavity, then the inner surface diverges outwardly to a maximum diameter less than the maximum diameter in the first portion an then converges inwardly forming a closed surface for the internal cavity opposite the aperture and forming a second portion of the internal cavity, the closed surface of the second portion is spaced inwardly from said second surface located opposite said aperture, and said inner surface defines said inwardly projecting annular rib separating said first and second portions of said internal cavity.

4. Mold for manufacturing a mamma prosthesis with an internal cavity, the mamma prosthesis having a first surface shaped to fit against the body of the wearer and a second surface having a configuration corresponding to the shape of a natural mamma, said mold comprising a lower mold member having a dish-shaped surface for forming the second surface of the mamma prosthesis, an upper mold member engageable with said lower mold member and said upper mold member having a surface for forming the first surface of the mamma prosthesis, said lower mold member and upper mold member combining to form a mold cavity, said upper mold member having a passageway therethrough opening into the mold cavity, wherein the improvement comprises a core positioned within the passageway in said upper mold member and extending therefrom into the mold cavity, an annular body mounted on said core within the mold cavity and extending laterally therefrom, the surface of said annular body disposed in spaced relation to the surfaces of said lower mold member and upper mold member which define the mold cavity, said annular body comprises a pair of interconnected annular ribs projecting laterally from said core and said pair of ribs comprises a first rib closer to said upper mold member and a second rib on the opposite side of said first rib from said upper mold member, said first and second ribs interconnected adjacent said core and spaced apart laterally outwardly from said core, said first and second ribs disposed in spaced relation to the surface of said lower mold member defining the mold cavity, said first and second ribs defining the internal cavity within the mamma prosthesis.

* * * * *